United States Patent
Gillet et al.

(10) Patent No.: US 6,624,322 B1
(45) Date of Patent: Sep. 23, 2003

(54) METHOD FOR PREPARING β-PHOSPHOROUS NITROXIDE RADICALS

(75) Inventors: Jean-Philippe Gillet, Brignais (FR); Olivier Guerret, Marcy l'Etoile (FR); Paul Tordo, Marseilles (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/869,911

(22) PCT Filed: Dec. 22, 1999

(86) PCT No.: PCT/FR99/03255

§ 371 (c)(1),
(2), (4) Date: Nov. 9, 2001

(87) PCT Pub. No.: WO00/40526

PCT Pub. Date: Jul. 13, 2000

(30) Foreign Application Priority Data

Jan. 8, 1999 (FR) ............................................ 99 00127

(51) Int. Cl.[7] .................................................. C07F 9/02
(52) U.S. Cl. ............................ 558/166; 568/14; 568/12
(58) Field of Search ..................... 558/73, 166; 568/12, 568/14

(56) References Cited

U.S. PATENT DOCUMENTS 4,990,617 A * 2/1991 Boswell et al. ............. 540/477
5,087,752 A 2/1992 Murray et al.
5,218,116 A 6/1993 Neri et al.
6,255,448 B1 * 7/2001 Grimaldi et al. ............ 528/176

FOREIGN PATENT DOCUMENTS

WO 9624620 8/1996
WO 9626205 8/1996

OTHER PUBLICATIONS

Grimaldi S. et al.: "Synthesis and applications to living free radical polymerization of a new class of nitoxyl radicals" POLYM.PREPR., 1997 vol. 38, p. 651–652.

Le Mercier et al.: "Synthesis of nitroxides and alkoxyamines used in controlled/living" radical polymerization POLYM PREPR., 1999 vol. 40, p. 403–404.

* cited by examiner

*Primary Examiner*—Jean F. Vollano
(74) *Attorney, Agent, or Firm*—Millen, White, Zelano & Branigan, P.C.

(57) ABSTRACT

The invention concerns a method for preparing β-phosphorous nitroxide radicals which comprises preparing in a first step an aminophosphonate by reacting a carbonyl compound, a primary amine and a phosphorous compound, then in a second step in oxidizing said aminophosphonate using on-halogenated organic peracids in a two-phase organic water/solvent medium with a buffered aqueous phase with a pH ranging between 5 and 12.

32 Claims, No Drawings

METHOD FOR PREPARING β-PHOSPHOROUS NITROXIDE RADICALS

This application is the national stage of PCT FR 09/03255 filed Dec. 22, 1999, now WO 00/040526.

A subject matter of the present invention is a process for the preparation of β-phosphorated nitroxide radicals of formula:

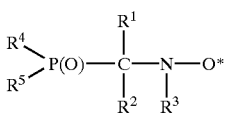
(I)

in which $R^1$, $R^2$, $R^3$, $R^4$ and $R^5$ will be defined subsequently. These compounds are used in particular as regulators of radical polymerization.

These compounds can be obtained in particular by the oxidation of N-alkylaminophosphonates of formula:

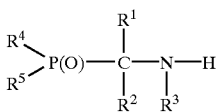
(II)

The N-alkylaminophosphonates (II) can be obtained in a known way by reacting a carbonyl compound $R^1R^2C(O)$, a primary amine $R^3NH_2$ and a phosphorus compound $HP(O)R^4R^5$ having a mobile hydrogen according to a Mannich-type reaction:

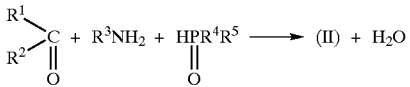

A process is disclosed in international patent application WO 96/24620 which consists in reacting, in a first stage, a carbonyl compound $R^1R^2C(O)$ with a primary amine $R^3NH_2$ according to a carbonyl compound/primary amine molar ratio substantially equal to 1 and then, in a second stage, in adding, to the compound obtained in the first stage, a phosphorus compound $HP(O)R^4R^5$ according to a phosphorus compound/product obtained in the first stage molar ratio ranging from 1.5 to 2.5, indeed even more. There are several disadvantages to this way of proceeding.

Thus, the water formed in the first stage during the reaction of the carbonyl compound with the primary amine which results in the formation of an imine according to the scheme:

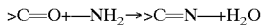

is not removed before the addition of the phosphorus compound, which may be of such a nature as to result in a possible hydrolysis of said phosphorus compound, in particular when the latter is a phosphite.

In addition, the use of a very large excess of phosphorus compound (150% to 250%, indeed even more) with respect to the compound obtained in the first stage (imine) is prohibitory for an industrial process.

Furthermore, this excess, in addition to the fact of the difficulties in removing it, is of such a nature as to generate numerous impurities by reaction with, in particular, the unconverted carbonyl compound to result in hydroxyphosphonates (>C(OH)—P(O)<) in the case where the phosphorus compound used is a phosphite. This excess of phosphorus compound can also result in the formation of heavy products resulting from the reaction between (II), the carbonyl compound and the excess phosphorus compound $HP(O)R^4R^5$.

All these impurities liable to be present in the crude product (II) make the purification of the N-alkylaminophosphonate (II) difficult and consequently render its subsequent use difficult.

The β-phosphorated nitroxide (I) can be obtained by oxidation of the N-alkylaminophosphonate (II) by replacing the hydrogen of >N—H with an oxygen atom.

This oxidation can be carried out according to various techniques known to a person skilled in the art. A few appropriate techniques are listed below in a nonexhaustive fashion:

reaction of a secondary amine with aqueous hydrogen peroxide solution in the presence of a solid catalyst (titanium silicalite), the principle of which is disclosed in patent U.S. Pat. No. 5,218,116;

reaction of a secondary amine with a dioxirane or its carbonyl precursors in combination with oxone®, the technique of which is disclosed in patent U.S. Pat. No. 5,087,752, reaction of a secondary amine with metachloroperbenzoic acid, according to a protocol described in the Journal of the American Chemical Society, 1967, 89 (12), pages 3055–3056.

According to international application WO 96/24620, diethyl 2,2-dimethyl-1-(1,1-dimethylethylamino) propylphosphonate could only be efficiently oxidized by means of meta-chloroperbenzoic acid (mCPBA) according to a protocol which consists in introducing the mCPBA, in solution in $CH_2Cl_2$, into a $CH_2Cl_2$ solution of the above-mentioned aminophosphonate. The β-phosphorated nitroxide obtained is purified by passing through a column of silica gel, which involves the use of a large volume of elution solvent.

This way of operating can only be applied to the preparation of small amounts of (I). In addition, the analysis of this product by HPLC has shown that this technique results in nitroxides with a purity of less than 80%.

In order to improve the process for the oxidation of the aminophosphonate (II) by mCPBA, the assignee of the present application has carried out the preliminary drying of the technical mCPBA, on the one hand, and optimized the mCPBA/aminophosphonate molar ratio, on the other hand.

Although a satisfactory yield of β-phosphorated nitroxide is obtained, this way of operating produces amounts of effluents (metachlorobenzoic acid salt) which are difficult to remove.

Furthermore, even the optimized use of mCPBA does not make possible viable translocation to the industrial scale.

The applicant has found that, by using nonhalogenated organic peracids in a water/organic solvent two-phase medium with an aqueous phase buffered at a pH ranging from 5 to 12, it can oxidize aminophosphonates (II) to β-phosphorated nitroxides (I) while significantly reducing the manufacturing costs and while generating effluents which can be easily removed.

A subject matter of the present invention is thus a process for the manufacture of compounds of general formula:

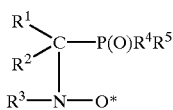

(I)

in which $R^1$ and $R^2$, which are identical or different, represent a hydrogen atom, a linear, branched or cyclic alkyl radical having a number of carbon atoms ranging from 1 to 10, an aryl radical, or an aralkyl radical having a number of carbon atoms ranging from 1 to 10, or else $R^1$ and $R^2$ are connected to one another so as to form a ring which includes the carbon atom carrying said $R^1$ and $R^2$ said ring having a number of carbon atoms, including the carbon carrying the $R^1$ and $R^2$ radicals, ranging from 3 to 8; $R^3$ represents a linear or branched and saturated or unsaturated hydrocarbonaceous radical which can comprise at least one ring, said radical having a number of carbon atoms ranging from 1 to 30; and $R^4$ and $R^5$, which are identical or different, represent a linear or branched alkyl radical having a number of carbon atoms ranging from 1 to 20 or a cycloalkyl, aryl, alkoxyl, aryloxyl, aralkyloxyl, perfluoroalkyl, aralkyl, dialkyl- or diarylamino, alkylarylamino or thioalkyl radical, or else $R^4$ and $R^5$ are connected to one another so as to form a ring which includes the phosphorus atom, said heterocycle having a number of carbon atoms ranging from 2 to 4 and being able in addition to comprise one or more oxygen, sulfur or nitrogen atoms;

said process consisting in oxidizing an aminophosphonate of formula

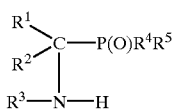

(II)

obtained by reaction of a carbonyl compound $R^1R^2C(O)$, of a primary amine $R^3NH_2$ and of a phosphorus compound $HP(O)R^4R^5$, $R^1$, $R^2$, $R^3$, $R^4$ and $R^5$ having the meanings given above; said process being characterized in that it consists first in preparing and optionally in isolating the compound II and then subsequently in oxidizing it by carrying out the following (successive) stages:

a) a carbonyl compound $R^1R^2C(O)$ is reacted with a primary amine $R^3NH_2$ according to an $R^1R^2C(O)/R^3NH_2$ molar ratio of between 0.8 and 1.5 and preferably between 0.9 and 1.1 at a temperature of between 0° C. and 120° C. and a pressure ranging from 1 to 10 bar; then the water formed is removed from the reaction medium;

b) the compound obtained in a) is reacted with a phosphorus compound $HP(O)R^4R^5$ used according to an $HP(O)R^4R^5$/compound a) molar ratio at most equal to 1.5 and preferably of between 1 and 1.5 at a temperature of between 0° C. and 120° C.;

c) an acidic treatment of the reaction medium obtained in b) is carried out, an organic solvent is subsequently added, separation by settling is carried out, the aqueous phase is recovered and then a basic treatment of said aqueous phase is carried out;

d) the aminophosphonate is extracted by means of an organic solvent identical to that used previously in c);

e) said solvent is then completely removed and said aminophosphorate (II) is isolated and is oxidized to β-phosphorated nitroxide according to the following stages:

$a^1$) the aminophosphonate (II) obtained in e) is dissolved in a water-immiscible organic solvent, then;

$b^1$) subsequently, an amount of non-halogenated organic peracid, according to a peracid/aminophosphonate (II) molar ratio ranging from 1.5 to 2.5, and a sufficient amount of a basic aqueous solution of an alkali metal carbonate or hydrogencarbonate or of an alkaline earth metal carbonate or hydrogencarbonate or alternatively of an ammonia solution to produce a pH ranging from 5 to 12 and preferably ranging from 6 to 9 are simultaneously added with vigorous stirring, at a temperature of between −10° C. and +40° C. and preferably of between −5° C. and +30° C., to the medium thus obtained, until the aminophosphonate (II) has been completely converted;

$c^1$) the organic phase is then recovered by simple separation by settling and the β-phosphorated nitroxide is isolated by evaporation of the organic solvent under reduced pressure.

The purity of the β-phosphorated nitroxide obtained can be improved by flash distillation under reduced pressure or by low temperature crystallization.

According to an alternative form of the process of the present invention, it is possible not to isolate the aminophosphonate (II) and to carry out the oxidation on the aqueous phase obtained in c), which comprises the aminophosphonate hydrochloride.

Should that arise, the procedure is thus carried out in the following way:

after having carried out the acidic treatment of the reaction medium obtained in b) and then added a water-immiscible organic solvent, the aqueous phase is separated by settling, an organic solvent is added to the aqueous phase and then stages $b^1$) and $c^1$) as described above are carried out.

Mention will be made, by way of illustration of carbonyl compounds $R^1R^2C(O)$ which can be used according to the present invention, of trimethylacetaldehyde (pivalaldehyde), isobutyraldehyde, cyclohexanecarboxyaldehyde, diethyl ketone, dibutyl ketone, methyl ethyl ketone, cyclohexanone, 4-tert-butylcyclohexanone or α-tetralone.

Mention will be made, by way of illustration of primary amines $R^3$—$NH_2$ which can be used according to the present invention, of methylamine, ethylamine, propylamine, isopropylamine, tert-butylamine, diphenylmethylamine, triphenylmethylamine, aniline, α-naphthylamine, benzylamine, 1-phenylethylamine, cyclohexylamine or cyclopentylamine.

Use will preferably be made of tert-butylamine, isopropylamine, diphenylmethylamine, 1-phenylethylamine or cyclohexylamine.

The reaction between the carbonyl compound $R^1R^2C(O)$ and the amine $R^3NH_2$ (stage a) is carried out with vigorous stirring at a temperature of between 0° C. and 120° C. and preferably at a temperature of between 0° C. and 60° C. The reaction is generally carried out at a pressure of between 1 bar and 10 bar, preferably at atmospheric pressure, and under an inert gas atmosphere, such as nitrogen or argon. The reaction time can vary within wide limits. It depends on the reactivity of the amine employed. The complete conversion of the carbonyl compound $R^1R^2C(O)$ can be confirmed by chromatographic (GC) analysis.

On completion of the reaction, stirring is halted and the reaction medium is allowed to separate by settling. Separation by settling is generally rapid. The aqueous phase, consisting virtually entirely of the water formed during the reaction between the carbonyl compound and the primary amine which results in the imine (III), according to the scheme:

(III)

is subsequently removed.

The removal of the water can be completed by the addition of a dehydrating agent, such as a molecular sieve, to the phase which has been separated by settling or alternatively azeotropic distillation can be carried out.

The imine (III) obtained in stage a) is reacted with a compound $HP(O)R^4R^5$ (stage b)).

Mention will be made, by way of illustration of phosphorus compounds $HP(O)R^4R^5$ which can be used according to the present invention, of dimethyl phosphite, diethyl phosphite, n-propyl phosphite, dibenzyl phosphite, diisopropyl phosphite, di(n-dodecyl)phosphite; diphenylphosphine oxide or dibenzylphosphine oxide.

The reaction between the phosphorus compound $HP(O)R^4R^5$ and the imine (III) obtained in stage a) is carried out with vigorous stirring at a temperature of between 0° C. and 120° C. and preferably at a temperature of between 10° C. and 80° C. As in stage a), the reaction is carried out under an inert gas atmosphere and preferably at atmospheric pressure.

Use is made of a molar excess of phosphorus compound $HP(O)R^4R^5$ with respect to the imine obtained in stage a) at most equal to 50% and preferably of an excess which is as low as possible, indeed even zero phosphorus compound/ imine (III) molar ratio equal to 1).

The reaction medium is kept stirred for a time which can vary within wide limits; this time is preferably at most equal to 25 hours.

The reaction medium is subsequently acidified (stage c)) with an aqueous hydrochloric acid solution.

The concentration by weight of HCl is at most equal to 20% and preferably between 5% and 15%. This acidification is preferably carried out at a temperature of between 0° C. and 20° C. and preferably at a temperature in the region of 10° C.

When the pH of the reaction medium is less than 3, a first extraction is carried out which consists in removing the organic impurities and unconverted reactants with an organic solvent which is a good solvent of the impurities. Methylene chloride ($CH_2Cl_2$) will advantageously be used.

Subsequently, the acidic aqueous phase (comprising the aminophosphonate hydrochloride) is separated by settling and is subjected to a basic treatment.

This acidic aqueous phase is preferably treated with an aqueous solution of an alkali metal carbonate or hydrogencarbonate, such as $K_2CO_3$, $NaHCO_3$, $KHCO_3$ or $Na_2CO_3$, or with an ammonia solution.

A second extraction (stage d)) of the released aminophosphonate (II) is subsequently carried out with the same solvent used in stage c).

The organic phase is advantageously washed with pure water and then concentrated under reduced pressure.

A virtually pure aminophosphonate (II) is obtained.

The oxidation of the aminophosphonate (II) to the nitroxide (I) is carried out according to stages $a^1$) to $c^1$) as described above.

Mention will be made, by way of illustration of organic solvents which can be used according to the present invention in stages $a^1$) to $c^1$), of aliphatic hydrocarbons, such as pentane, heptane or cyclohexane;

chlorinated solvents, such as $CH_2Cl_2$; esters of aliphatic acids, such as ethyl acetate or ethyl propionate, or a mixture of at least two of the abovementioned solvents.

Mention will be made, by way of illustration of nonhalogenated organic peracids which can be used according to the present invention, of peracetic acid, perpropionic acid or perbutanoic acid.

The compounds (I) can be identified by elemental analysis, HPLC, IR and EPR.

The compounds (II) obtained according to the invention can be identified by proton, $^{13}C$ and $^{31}P$ NMR, by IR and by elemental analysis.

The compounds obtained according to the process of the present invention have a sufficient purity to be used as regulators of radical polymerizations.

The process according to the present invention exhibits the advantage of resulting in high yields of β-phosphorated nitroxide radicals.

The examples which follow illustrate the invention.

EXAMPLE 1

Preparation of Diethyl 2,2-Dimethyl-1-(1,1-dimethyl-ethylamino)propylphosphonate, the Precursor of N-tert-Butyl-1-diethylphosphono-2,2-dimethylpropyl Nitroxide 173 g of pivalaldehyde (approximately 97%), i.e. 1.95 mol, are introduced into 2.5 l Schott reactor equipped with an anchor stirrer, a dropping funnel, a temperature probe, a water-cooled reflux condenser, a heating jacket and a system for inerting with nitrogen and are cooled to 10° C. under nitrogen. Subsequently, 153.5 g of 98% tert-butylamine, i.e. 2.06 mol, are run in over 70 minutes. After the tert-butylamine has finished being run in, the mixture is heated at 35° C. for 2 hours. The complete conversion of the aldehyde is subsequently confirmed by GC. Stirring is halted and the separation by settling is observed of a lower aqueous phase, which is withdrawn from the reaction medium.

Subsequently, 411 g (2.91 mol, i.e. a molar excess of 49%) of diethyl phosphite are added over 20 minutes at 20° C., still under a nitrogen atmosphere. The reaction medium is subsequently stirred for 20 hours at 40° C. The reaction is halted when it is found that all the intermediate imine has been consumed.

Subsequently, the crude reaction product recovered is treated. This crude product is a slightly yellowish liquid.

A 5% solution of HCl in water is used to acidify to pH 3 while keeping the medium at 10° C. As the reaction is exothermic, cooling is carried out with ice.

The organic impurities are extracted with methylene chloride. A colorless aqueous phase comprising the aminophosphonate hydrochloride is thus recovered and is rebasified with a saturated $KHCO_3$ solution to a pH of 7.8.

The aminophosphonate is subsequently extracted with $CH_2Cl_2$. The organic phase from this extraction is dried and then concentrated on a rotary evaporator. 360 g of a colorless liquid are thus recovered with an aminophosphonate purity of greater than 99%. The reaction yield is 66% with respect to the pivalaldehyde introduced.

EXAMPLE 2

Preparation of Diethyl 2,2-Dimethyl-1-(1,1-dimethyl-ethylamino)propylphosphonate at the Semi-Industrial Stage 892 g (10 mol) of pivalaldehyde are charged to an 8.4 l glass reactor equipped as above. 751 g (10 mol) of tert-butylamine are subsequently run in over 57 minutes while maintaining the temperature of the reaction medium in the region of 10° C. After reacting for 2 hours at 40° C., stirring is halted. An aqueous phase separates on settling and is withdrawn from the reactor (184 g).

2 133 g (15 mol) of diethyl phosphite are subsequently added over 55 minutes. The reaction medium is stirred at ambient temperature for 19 hours.

3 511 g of a crude reaction product comprising 68% of aminophosphonate are recovered.

The crude reaction product is subsequently purified by an acid/base treatment. 1 796 g of aminophosphonate with a purity >96% are obtained. The reaction yield after purification is 62%.

EXAMPLE 3 (NOT IN ACCORDANCE WITH THE INVENTION)

Preparation of N-tert-Butyl-1-diethylphosphono-2,2-dimethylpropyl Nitroxide by Oxidation of Diethyl 2,2-Dimethyl-1-(1,1-dimethylamino) propylphosphonate (Hereinafter Aminophosphonate) With Metachloroperbenzoic Acid (mCPBA)

304 g (1.21 mol) of mCPBA are charged to 4,018 g (3 l) of $CH_2Cl_2$ in an 8.4 l glass reactor equipped as in Example 1. After the peracid has completely dissolved, 66.3 g of an aqueous phase are separated by settling. The organic solution of mCPBA is dried by means of a 4 Å molecular sieve. 225.8 g (0.769 mol) of aminophosphonate as obtained in Example 1 are then added dropwise to the reaction medium, which is maintained at 10° C. After reacting for 2 hours, the mixture is neutralized by means of a saturated aqueous $KHCO_3$ solution (1,537 g) at ambient temperature.

The orangey organic phase is isolated, washed with water and then concentrated under reduced pressure.

207.7 g of N-tert-butyl-1-diethylphosphono-2,2-dimethylpropyl nitroxide are obtained with a purity equal to 77%. The reaction yield with respect to the aminophosphonate is 71%.

EXAMPLE 4 (ACCORDING TO THE INVENTION)

Preparation of N-tert-Butyl-1-diethylphosphono-2,2-dimethylpropyl Nitroxide (Hereinafter Nitroxide) by Oxidation of Diethyl 2,2-Dimethyl-1-(1,1-dimethylethylamino)propylphosphonate (Hereinafter Aminophosphonate) With Peracetic Acid in a Two-Phase Medium 5 g of aminophosphonate as obtained in Example 1 are diluted in 300 ml of $CH_2Cl_2$ in a reactor equipped with two dropping funnels and a pH meter probe. 60 ml of water are added and the mixture is kept subject to vigorous mechanical stirring. Two equivalents of peracetic acid at 15% in acetic acid, i.e. 17.2 g, were prepared in a dropping funnel. 7.8 g of potassium bicarbonate, dissolved in 140 ml of water, were prepared in the other. The two reactants are run in so as to maintain the pH of the aqueous phase at between 5 and 7. An evolution of gas ($CO_2$) is observed. The solution gradually turns yellow and the level of active oxygen in each phase is regularly monitored. After 24 h, the organic phase is orange and gas evolution has entirely ceased. The organic phase is recovered by separating by settling and the solvent is evaporated. The crude nitroxide exists in the form of a dark orange oil (4.1 g), the purity of which is 89%. The overall yield is 70%.

EXAMPLE 5 (ACCORDING TO THE INVENTION)

Preparation of N-tert-Butyl-1-diethylphosphono-2,2-dimethylpropyl Nitroxide (Hereinafter Nitroxide) by Oxidation of Diethyl 2,2-Dimethyl-1-(1,1-dimethylethylamino)propylphosphonate (Hereinafter Aminophosphonate) With Perpropionic Acid in a Two-Phase Medium 5 g of aminophosphonate (0.017 mol) as obtained according to Example 1 are diluted in 100 ml of ethyl acetate in a reactor equipped with two dropping funnels, a mechanical stirrer and a pH meter probe. 60 ml of water are added and the mixture is kept subject to vigorous stirring. Subsequently, 13.77 g of 20% by weight perpropionic acid (0.0307 mol) in ethyl propionate and an 8.5% by weight aqueous $K_2CO_3$ solution. (13 g of $K_2CO_3$ in 140 ml of water) are slowly and simultaneously introduced with stirring, so as to maintain the pH of the aqueous phase at between 5 and 7. An evolution of gas ($CO_2$) is observed. The solution gradually turns yellow and the level of active oxygen in each phase is regularly monitored. After 16 h, the organic phase is orange and gas evolution has entirely ceased. The organic phase is recovered by separating by settling and the solvent is evaporated. The crude nitroxide exists in the form of a dark orange oil (4.6 g), the purity of which is equal to 62.5%. The β-phosphorated nitroxide yield is 54%.

EXAMPLE 6 (NOT IN ACCORDANCE WITH THE INVENTION)

Preparation of N-tert-Butyl-1-diethylphosphono-2,2-dimethylpropyl Nitroxide (Hereinafter Nitroxide) by Oxidation of Diethyl 2,2-Dimethyl-1-(1,1-dimethylethylamino)propylphosphonate (Hereinafter Aminophosphonate) With Peracetic Acid 8.3 g of 32% peracetic acid, 55 g of $CH_2Cl_2$ and 10 g of aminophosphonate as obtained according to Example 1 are mixed in a 250 ml round-bottomed flask. This mixture is kept stirred for 24 hours. The solution is subsequently neutralized using a saturated potassium carbonate solution and the organic phase is recovered.

After evaporating the dichloromethane, 1.2 g of an orange liquid are obtained (yield of less than 8.7%).

EXAMPLE 7 (ACCORDING TO THE INVENTION)

Preparation of N-tert-Butyl-1-diethylphosphono-2,2-dimethylpropyl Nitroxide (Hereinafter Nitroxide) by Oxidation of Diethyl 2,2-Dimethyl-1-(1,1-dimethylethylamino)propylphosphonate (Hereinafter Aminophosphonate) With Peracetic Acid in a Two-Phase Medium Without Isolation of the Aminophosphonate 11.18 g of pivalaldehyde are introduced into a 1 liter round-bottomed flask equipped with a mechanical stirrer, two dropping funnels, a reflux condenser, a bottom valve and a nitrogen inlet, 9.5 g of tert-butylamine being slowly added to the pivalaldehyde. The mixture is left to stir at 35° C. for 1 h 30 and is then cooled. The water formed is separated by settling and removed via the bottom valve. 28.1 g of diethyl phosphite are then added and the mixture is left to stir at 40° C. for 17 h. After cooling, 130 g of a 5% by weight aqueous HCl solution are slowly added at 0° C. The solution is washed with $CH_2Cl_2$ to remove the impurities. The aqueous solution of aminophosphonate hydrochloride thus obtained is subsequently used as is for conversion to the nitroxide.

300 g of $CH_2Cl_2$ are added to this solution and vigorous stirring is maintained. 61 g of a 32% by weight solution of peracetic acid in acetic acid are subsequently added slowly and, at the same time, the potassium carbonate solution is run in, so as to bring the pH to and to maintain it at between 5 and 7. After 4 h, the organic phase is dark orange and the reaction is halted.

After extracting and washing the organic phase, the dichloromethane is evaporated under reduced pressure, which makes it possible to obtain 15 g of nitroxide.

What is claimed is:

1. A process for the manufacture of at least one compound of formula I:

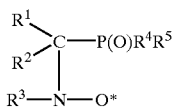

(I)

in which $R^1$ and $R^2$, which are identical or different, represent a hydrogen atom, a linear, branched or cyclic alkyl radical having 1 to 10 carbon atoms, an aryl radical, or an aralkyl radical having 1 to 10 carbon atoms or else $R^1$ and $R^2$ are connected to one another so as to form a ring, said ring having 3 to 8 carbon atoms, $R^3$ represents a linear, branched or cyclic, saturated or unsaturated, hydrocarbon radical having 1 to 30 carbon atoms; and $R^4$ and $R^5$, which are identical or different, represent a linear or branched alkyl radical having 1 to 20 carbon atoms or a cycloalkyl, aryl, alkoxyl, aryloxyl, aralkyloxyl, perfluoroalkyl, aralkyl, dialkyl- or diarylamino, alkylarylamino or thioalkyl radical, or $R^4$ and $R^5$ are connected to one another so as to form a heterocyclic ring which includes the phosphorus atom, said heterocyclic ring having 2–4 carbon atoms and optionally containing one or more oxygen, sulfur or nitrogen hetero atoms;

said process comprising forming and oxidizing a β-phosphoroamine of formula II:

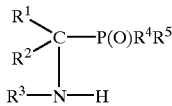

(II)

wherein said forming of β-phosphoroamine (II) comprises the following stages:

a) a carbonyl compound $R^1R^2C(O)$ is reacted with a primary amine $R^3NH_2$ with an $R^1R^2C(O)/R^3NH_2$ molar ratio of between 0.8 and 1.5, at a temperature of between 0° C. and 120° C., and a pressure ranging from 1 to 10 bar; the resultant water formed is removed from the reaction medium and an imine of the formula $R^1R^2C=NR^3$ (III) is obtained;

b) the imine of formula III is reacted with a phosphorus compound $HP(O)R^4R^5$ with an $HP(O)R^4R^5$/imine molar ratio of at most equal to 1.5 at a temperature of between 0° C. and 120° C.;

c) an acidic treatment of the reaction medium obtained in b) is carried out, a water-immiscible organic solvent is subsequently added, a settled out resultant aqueous phase is recovered and then a basic treatment of said aqueous phase is carried out to form said β-phosphoroamine of formula II;

d) the resultant β-phosphoroamine of formula II is extracted from the aqueous phase with an organic solvent identical to that previously used in c);

e) said solvent is then completely removed and said β-phosphoroamine (II) is isolated and wherein said oxidizing of β-phosphoroamine to β-phosphorated nitroxide is conducted according to the following stages:

a¹) the β-phosphoroamine (II) obtained in e) is dissolved in a water-immiscible organic solvent to form an organic medium;

b¹) subsequently, an amount of non-halogenated organic peracid, according to a peracid/β-phosphoroamine (II) molar ratio ranging from 1.5 to 2.5, and a sufficient amount of a basic aqueous solution of an alkali metal carbonate or hydrogencarbonate or of an alkaline earth metal carbonate or hydrogencarbonate or alternatively of an ammonia solution to produce a pH ranging from 5 to 12 are simultaneously added with vigorous stirring, at a temperature of between −10° C. and +40° C., to the organic medium until the β-phosphoroamine (II) has been converted;

c¹) the organic phase is then separated and the resultant β-phosphorated nitroxide provided, or, alternatively, stages d), e), and a1) are omitted and, instead, a stage of adding a water-immiscible organic solvent to the β-phosphoroamine of formula II from stage c) to form an organic medium and then carrying out stages b1) and c1) are conducted.

2. The process as claimed in claim 1, wherein the alternative of omitting stages d), e), and a1) and, instead, a stage of adding a water-immiscible organic solvent to the β-phosphoroamine of formula II from stage c) to form an organic medium and then carrying out stages $b^1$) and $c^1$) is conducted.

3. The process as claimed in claim 1, wherein the HP(O)$R^4R^5$/imine compound molar ratio in stage b) is between 1 and 1.5

4. The process as claimed in claim 1, wherein the temperature of the reaction between the carbonyl compound $R^1R^2C(O)$ and the primary amine $R^3NH_2$ is between 0° C. and 60° C.

5. The process as claimed in claim 1, wherein the temperature of the reaction between the phosphorus compound HP(O)$R^4R^5$ and said imine (III) is between 10° C. and 80° C.

6. The process as claimed in claim 1, wherein the water immiscible organic solvent in stage ($a^1$) is methylene chloride.

7. The process as claimed in claim 1, wherein the water-immiscible organic solvent used in stage ($a^1$) is ethyl acetate.

8. The process as claimed in claim 1, wherein the amine $R^3NH_2$ is tert-butylamine, isopropylamine, diphenylmethylamine, 1-phenylethylamine or cyclohexylamine.

9. The process as claimed in claim 8, wherein the amine $R^3NH_2$ is tert-butylamine.

10. The process as claimed in claim 1, wherein the phosphorus compound HP(O)$R^4R^5$ is dimethyl phosphite, diethyl phosphite, n-propyl phosphite, diisopropyl phosphite dibenzyl phosphite diphenylphosphine oxide or dibenzyl phosphine oxide.

11. The process as claimed in claim 10, wherein the phosphorus compound HP(O)$R^4R^5$ is diethyl phosphite.

12. The process as claimed in claim 1, wherein the carbonyl compound $R^1R^2C(O)$ is pivalaldehyde, isobutyraldehyde, cyclohexanecarboxaldehyde or cyclohexanone.

13. The process as claimed in claim 12, wherein the carbonyl compound $R^1R^2C(O)$ is pivalaldehyde.

14. The process as claimed in claim 1, wherein the nonhalogenated organic peracid is peracetic acid or perpropionic acid.

15. The process as claimed in claim 2, wherein the $HP(O)R^4R^5$/imine compound molar ratio in stage b) is between 1 and 1.5.

16. The process as claimed in claim 2, wherein the temperature of the reaction between the carbonyl compound $R^1R^2C(O)$ and the primary amine $R^3NH_2$ is between 0° C. and 60° C.

17. The process as claimed in claim 2, wherein the temperature of the reaction between the phosphorus compound $HP(O)R^4R^5$ and the imine compound (III) is between 10° C. and 80° C.

18. The process as claimed in claim 2, wherein the water-immiscible organic solvent in stage ($a^1$) is methylene chloride.

19. The process as claimed in claim 2, wherein the water-immiscible organic solvent used in stage ($a^1$) is ethyl acetate.

20. The process as claimed in claim 2, wherein the amine $R^3NH_2$ is tert-butylamine, isopropylamine, diphenylmethylamine, 1-phenylethylamine or cyclohexylamine.

21. The process as claimed in claim 20, wherein the amine $R^3NH_2$ is tert-butylamine.

22. The process as claimed in claim 2, wherein the phosphorus derivative $HP(O)R^4R^5$ is dimethyl phosphate, diethyl phosphate, n-propyl phosphate, diisopropyl phosphite or dibenzyl phosphite.

23. The process as claimed in claim 22, wherein the phosphorus compound $HP(O)R^4R^5$ is diethyl phosphite.

24. The process as claimed in claim 2, wherein the carbonyl compound $R^1R^2C(O)$ is pivalaldehyde, isobutyraldehyde, cyclohexanecarboxaldehyde or cyclohexanone.

25. The process as claimed in claim 24, wherein the carbonyl compound $R^1R^2C(O)$ is pivalaldehyde.

26. The process as claimed in claim 2, wherein the nonhalogenated organic peracid is peracetic acid or perpropionic acid.

27. The process according to claim 1, wherein said β-phosphoroamine II is isolated in stage e) prior to conducting said oxidizing.

28. A process for the manufacture of at least one compound of formula I:

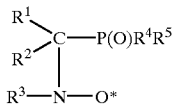

(I)

in which $R^1$ and $R^2$, which are identical or different, represent a hydrogen atom, a linear, branched or cyclic alkyl radical having 1 to 10 carbon atoms, an aryl radical, or an aralkyl radical having 1 to 10 carbon atoms or else $R^1$ and $R^2$ are connected to one another so as to form a ring, said ring having 3 to 8 carbon atoms, $R^3$ represents a linear, branched or cyclic, saturated or unsaturated, hydrocarbon radical having 1 to 30 carbon atoms; and $R^4$ and $R^5$, which are identical or different, represent a linear or branched alkyl radical having 1 to 20 carbon atoms or a cycloalkyl, aryl, alkoxyl, aryloxyl, aralkyloxyl, perfluoroalkyl, aralkyl, dialkyl- or diarylamino, alkylarylamino or thioalkyl radical, or $R^4$ and $R^5$ are connected to one another so as to form a heterocyclic ring which includes the phosphorus atom, said heterocyclic ring having 2–4 carbon atoms and optionally containing one or more oxygen, sulfur or nitrogen hetero atoms; said process comprising providing a medium comprising an aqueous phase, ethyl acetate, and a β-phosphoroamine of formula II:

(II)

and adding to said medium, an amount of non-halogenated organic peracid, according to a peracid/β-phosphoroamine (II) molar ratio ranging from 1.5 to 2.5, and a sufficient amount of a basic aqueous solution of an alkali metal carbonate or hydrogencarbonate or of an alkaline earth metal carbonate or hydrogencarbonate or alternatively of an ammonia solution to produce a pH ranging from 5 to 12 with vigorous stirring, at a temperature of between −10° C. and +40° C., to convert the β-phosphoroamine (II) to said compound of formula (I).

29. The process as claimed in claim 28, wherein the nonhalogenated organic peracid is peracetic acid or perpropionic acid.

30. A process for the manufacture of at least one compound of formula I:

(I)

in which $R^1$ and $R^2$, which are identical or different, represent a hydrogen atom, a linear, branched or cyclic alkyl radical having 1 to 10 carbon atoms, an aryl radical, or an aralkyl radical having 1 to 10 carbon atoms or else $R^1$ and $R^2$ are connected to one another so as to form a ring, said ring having 3 to 8 carbon atoms, $R^3$ represents a linear, branched or cyclic, saturated or unsaturated, hydrocarbon radical having 1 to 30 carbon atoms; and $R^4$ and $R^5$, which are identical or different, represent a linear or branched alkyl radical having 1 to 20 carbon atoms or a cycloalkyl, aryl, alkoxyl, aryloxyl, aralkyloxyl, perfluoroalkyl, aralkyl, dialkyl- or diarylamino, alkylarylamino or thioalkyl radical, or $R^4$ and $R^5$ are connected to one another so as to form a heterocyclic ring which includes the phosphorus atom, said heterocyclic ring having 2–4 carbon atoms and optionally containing one or more oxygen, sulfur or nitrogen hetero atoms;

said process comprising providing a β-phosphoroamine of formula II:

(II)

and oxidizing said β-phosphoroamine to β-phosphorated nitroxide according to the following stages:

a¹) dissolving the β-phosphoroamine (II) in a water-immiscible organic solvent to form an organic medium; and b¹) subsequently, simultaneously adding to said organic medium, an amount of non-halogenated organic peracid, according to a peracid/β-phosphoroamine (II) molar ratio ranging from 1.5 to 2.5, and a sufficient amount of a basic aqueous solution of an alkali metal carbonate or hydrogencarbonate or of an alkaline earth metal carbonate or hydrogencarbonate or alternatively of an ammonia solution to produce a pH ranging from 5 to 12, with vigorous stirring, at a temperature of between −10° C. and +40° C., to convert the β-phosphoroamine (II) to said compound of formula I.

31. The process as claimed in claim 30, wherein the nonhalogenated organic peracid is peracetic acid or perpropionic acid.

32. The process of claim 1, wherein the resultant β-phosphorated nitroxide from stage c¹) is isolated by rotoevaporation or by evaporation of the organic solvent under reduced pressure.

* * * * *

UNITED STATES PATENT AND TRADEMARK OFFICE
CERTIFICATE OF CORRECTION

PATENT NO. : 6,624,322 B1
DATED : September 23, 2003
INVENTOR(S) : Jean-Philippe Gillet It is certified that error appears in the above-identified patent and that said Letters Patent is hereby corrected as shown below:

Column 14,
Line 45, reads "$R^1$" should read -- $R^2$ --

Signed and Sealed this

Eleventh Day of January, 2005

JON W. DUDAS
*Director of the United States Patent and Trademark Office*